United States Patent [19]

Cier et al.

[11] 3,952,027

[45] Apr. 20, 1976

[54] ALICYCLIC COMPOUNDS AND PROCESS FOR PREPARING THE SAME

[75] Inventors: André Cier, Neuilly-sur-Seine; Stephan Gero, Ablon; Alain Olesker; Jean Leboul, both of Gif-sur-Yvette, all of France

[73] Assignee: Labaz, Paris, France

[22] Filed: Jan. 31, 1975

[21] Appl. No.: 545,799

[52] U.S. Cl. .............................. 260/349; 260/563 R
[51] Int. Cl.² ........................................ C07C 117/00
[58] Field of Search ..................................... 260/349

[56] References Cited
UNITED STATES PATENTS 3,496,196  2/1970  Suami et al. .................... 260/349

Primary Examiner—Elbert L. Roberts
Assistant Examiner—Cary Owens
Attorney, Agent, or Firm—Mason, Kolehmainen, Rathburn & Wyss

[57] ABSTRACT

Cyclohexanediol derivatives of the general formula:

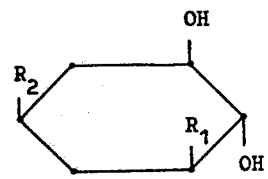

wherein $R_1$ and $R_2$, which are identical, each represent a $N_3$ or $NH_2$ group, and the acid addition salts of the derivative containing two $NH_2$ groups.

These compounds are useful as intermediate products for the preparation, for example, of synthetic antibiotics.

1 Claim, No Drawings

ALICYCLIC COMPOUNDS AND PROCESS FOR PREPARING THE SAME

This invention relates to alicyclic compounds and is concerned with novel cyclohexanediol derivatives and to a process for preparing the same.

The cyclohexanediol derivatives with which the invention is concerned are the compounds represented by the general formula:

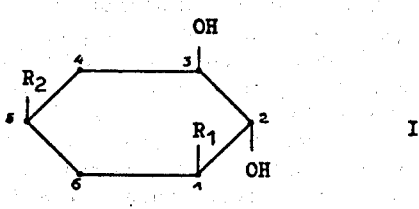

wherein $R_1$ and $R_2$, which are identical, each represent a $N_3$ or $NH_2$ group.

These two cyclohexanediol derivatives correspond to the following chemical terminology:

1D-(1,3,5/2)-1,5-diazido-2,3-cyclohexanediol and
1D-(1,3,5/2)-1,5-diamino-2,3-cyclohexanediol The present invention also includes within its scope the acid addition salts of the diaminocyclitol of formula I namely that compound of formula I which contains two $NH_2$ groups. These acid addition salts may be either single (mono-) i.e. formed from one molecule of the diaminocyclitol and one molecule of acid or double (di-) i.e. formed from one molecule of diaminocyclitol and two molecules of acid.

Another object of the present invention is to provide a method of use of the novel diazide of formula I as a particularly valuable intermediate product.

The nomenclature used in this specification is that presented under Recommended Rules by the I.U.P.A.C. - I.U.B. Tentative Cyclitol Nomenclature Rules — Eur. J. Biochem. 5, 1, (1968).

The compound of formula I containing two $N_3$ groups may be prepared by heating in a suitable medium such as N,N-dimethylformamide or hexamethylphosphotriamide and in the presence of an alkali metal azide, for example sodium azide, a compound of the formula:

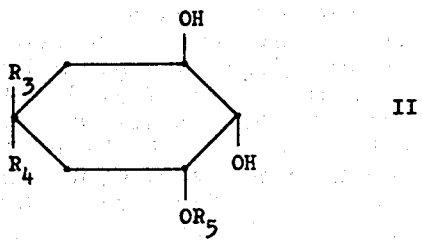

wherein $R_3$ represents a $N_3$ group when $R_4$ represents a hydrogen atom or $R_3$ represents a hydrogen atom when $R_4$ represents an alkane-sulphonyloxy group such as a methanesulphonyloxy group or an arenesulphonyloxy group such as a p-toluenesulphonyloxy or p-bromobenzenesulphonyloxy group and $R_5$ represents an alkanesulphonyl group such as a methanesulphonyl group or an arenesulphonyl group such as a p-toluenesulphonyl or p-bromobenzenesulphonyl group to obtain the required diazide of formula I.

The other compound of formula I, namely that containing two $NH_2$ groups, may be prepared by hydrogenating in an appropriate solvent such as methanol, ethanol, isopropanol, or hexamethylphosphotriamide and in the presence of a catalyst such as Raney's nickel, platinum oxide or palladium charcoal, the diazide of formula I, obtained by the process described hereabove, to provide the diaminocyclitol of formula I, which may then if desired, be treated with an appropriate acid such as hydrochloric or sulphuric acid to form an acid addition salt.

The compounds of formula II can be obtained by treating in an appropriate solvent, for example pyridine, an epoxide of the formula:

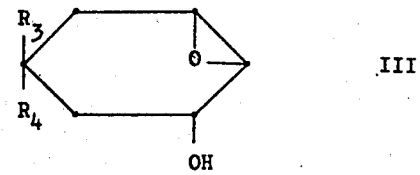

wherein $R_3$ and $R_4$ have the same meaning as in formula II, with a chloride of the formula:

$$R_5—Cl \qquad\qquad IV$$

wherein $R_5$ has the same meaning as in formula II, which provides the epoxide of the formula:

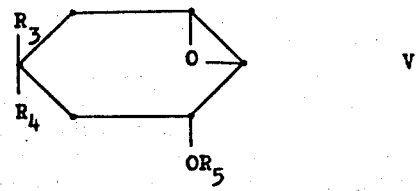

wherein $R_3$, $R_4$ and $R_5$ have the same meaning as in formula II.

The compound of formula V so obtained is then submitted to an acid treatment by heating for example, in an aqueous sulphuric acid solution which gives the required compound of formula II.

Amongst the compounds of formula III, 1L-2,3-anhydro-5-0-tosyl-1,2,3,5/0-cyclohexanetetrol and 1L-2,3-anhydro-(1,2,3/5)-5-azido-1,2,3-cyclohexanetriol are known compounds having been specifically described in Belgian Pat. No. 805,949 and in Deutsche Offenlegungsschrift No. 2,352,061.

The other compounds of formula III can be prepared by the same method as that described in the above-cited Belgian Patent and Deutsche Offenlegungsschrift for the preparation of the two derivatives of formula II previously cited.

It is known that antibiotics containing an aminocyclitol subunit such as gentamicin, can be obtained, following known procedures, by growing microorganisms in an appropriate nutrient medium containing assimilable sources of carbohydrate, nitrogen and inorganic salts. The microorganism used biosynthetizes the aminocyclitol subunit incorporated in the antibiotics so formed.

Similarly, it is known from U.S. Pat. No. 3,669,838 that mutants of those microorganisms "can be formed which lack the capacity to biosynthesize the aminocyclitol subunit but have the capacity to utilize an added aminocyclitol molecule to form an antibiotic. When the added aminocyclitol molecule is different than the aminocyclitol subunit present in the antibiotic produced by the unmutated microorganism, a new antibiotic is produced".

In this case, the aminocyclitol subunit is added to the nutrient medium in the presence of the mutated microorganism as described in the aforesaid U.S. Patent.

Thus, the diaminocyclitol of the invention will provide an extremely useful aminocyclitol subunit for the preparation of synthetic antibiotics, owing to the fact that the chemical structure of this diaminocyclitol contains a steric arrangement of amino and hydroxy groups which is analogous but nevertheless different from the natural diaminocyclitols, such as 2-deoxystreptamine, included in the molecular composition of antibiotics of the hybrimycin series.

However, the diaminocyclitol of the invention is not a very stable compound as it deteriorates fairly quickly. It cannot, therefore, be easily stored and consequently must be prepared immediately before use.

The diazide of formula I, on the other hand is easy to handle, very stable and can be stored for long periods of time which means that it offers the appreciable advantage of being immediately available when required without having to be prepared on every occasion when its use is indicated. For this reason, the diazide of formula I which may be used, for example, for the preparation of the corresponding diaminocyclitol of formula I and its salts, constitutes a very useful intermediate compound.

Moreover, the presence of the two azide groups in the diazide of formula I confers on this molecule a high degree of reactivity and in particular will enable subsequent reactions to be performed which would otherwise be impossible or at least very difficult.

As stated above, the diazide of formula I can be used, for example, for preparing the diaminocyclitol of the invention.

The method of preparation applied for this purpose in accordance with the invention consists of the catalytic reduction of the diazide corresponding to formula I and presents several advantages which render it admirably suitable for use on the industrial scale. The reduction operation in question can, in fact, be carried out without applying heat from an outside source and can be performed at atmospheric pressure. The operating conditions are most advantageous because they obviate the use of energy and the need to work under pressure which, of course, enhances the safety of the operator. Furthermore, the diaminocyclitol thus prepared is obtained without any impurities which renders unnecessary any subsequent operation of separation which is always so costly on the industrial scale.

Because the diazide of formula I can be converted to the corresponding diaminocyclitol or its salts without any difficulty and with good yield, this diaminocyclitol may be prepared from the diazide of formula I whenever required.

Thus owing to the fact that the novel diazide of formula I may be easily and rapidly converted to the corresponding diaminocyclitol, this latter compound may be considered to be available almost as readily as if it could be prepared and stored well in advance of its use.

The following Examples illustrate the invention:

EXAMPLE 1

Preparation of 1D-(1,3,5/2)-1,5-diazido-2,3-cyclohexanediol (Formula I)

a.
1L-2,3-anhydro-1,5-di-0-tosyl-1,2,3,5/0-cyclohexanetetrol (Formula V)

At a temperature of 0°C, 4g of tosyl chloride (p-toluenesulphonyl chloride) dissolved in 25 ml of pyridine were added drop-by-drop to a solution of 4g of 1L-2,3-anhydro-5-0-tosyl-1,2,3,5/0-cyclohexanetetrol in 20 ml of pyridine. The reaction medium was allowed to stand for 20 hours at 0°C and was then poured onto ice. The mixture was extracted several times with chloroform and the chloroformic extracts were washed with water. After drying on anhydrous sodium sulphate and evaporation of the chloroform and pyridine, a white foam was isolated which provided 4.3 g of crystals after crystallisation from methanol. The product so obtained was washed three times with 10 ml of methanol.

In this manner, analytical crystals of 1L-2,3-anhydro-1,5-di-0-tosyl-1,2,3,5/0-cyclohexanetetrol were obtained after recrystallisation from ethyl acetate.

M.P. 143.5°–145°C.

$[\alpha]_D^{25} = + 34°$ (c=1.93, chloroform).

At room temperature, the mother liquor of crystallisation from methanol was treated with 6 ml of a sodium methylate solution prepared from 2g of sodium in 75 ml of methanol. After several minutes, crystals precipitated. The mixture was allowed to stand for a further hour and then filtered.

In this way, a further 1.3g of the desired ditosylate were obtained, which finally represents 5.6 g of 1L-2,3-anhydro-1,5-di-0-tosyl-1,2,3,5/0-cyclohexanetetrol.

Total yield: 90 %.

b. 1L-1,5-di-0-tosyl-1,2,5/3-cyclohexanetetrol (Formula II)

In a flask containing 3.2g of 1L-2,3-anhydro-1,5-di-0-tosyl-1,2,3,5/0-cyclohexanetetrol, prepared as described hereabove, dissolved in 10 ml of 1,2-dimethoxy-ethane, there were added 50 ml of a 1.5 N aqueous solution of sulphuric acid.

The reaction medium was refluxed for 150 minutes and cooled to 0°C while a demixing phase appeared. The mixture was neutralised with an aqueous solution of sodium bicarbonate and then extracted with ethyl acetate. The organic phase was washed with water and dried on anhydrous sodium sulphate. After evaporation of the solvents, a white foam was obtained which provided 3.1g. of 1L-1,5-di-0-tosyl-1,2,5/3-cyclohexanetetrol after crystallisation from chloroform (yield: 90%). The analytical product melted at 121°–123°C after recrystallisation.

$[\alpha]_D^{25} = + 10°$ (c= 1, ethanol).

c. 1D-(1,3,5/2)-1,5-diazido-2,3-cyclohexanediol (Formula I)

To a mixture of 2.6g of sodium azide in 50 ml of N,N-dimethylformamide, were added 4.5g of 1L-1,5-di-0-tosyl-1,2,5/3-cyclohexanetetrol, prepared as hereabove described.

The black solution so obtained was refluxed for 2 hours, poured into iced water and them extracted with ethyl acetate. The organic phase was washed with water, dried on anhydrous sodium sulphate and the solvent was evaporated off. In this way, 1.92g of a black oil, which was very fluid, were isolated and partially discoloured by means of animal charcoal in ethanol.

In this manner, 1.2g of 1D-(1,3,5/2)-1,5-diazido-2,3-cyclohexanediol were obtained, in the form of beige crystals, after two successive recrystallisations from a chloroform/petroleum ether mixture. This represents a yield of 60 %.

M.P. 62°–63.5°C.

$[\alpha]_D^{25} = + 2° \pm 1$ (c=1, methanol).

EXAMPLE 2

Preparation of 1D-(1,3,5/2)-1,5-diamino-2,3-cyclohexanediol dihydrochloride

To a solution of 0.49g of 1D-(1,3,5/2)-1,5-diazido-2,3-cyclohexanediol, prepared as described hereabove in 25 ml of ethanol were added 2 ml of Raney's nickel (i.e. a catalyst of finely divided nickel obtained by dissolving out with alkali the aluminium from a nickel-aluminium alloy).

The reaction medium was hydrogenated for 5 hours. The catalyst was then separated out by filtration on Celite (a commercially available diatomaceous silica product, the word "Celite" being a registered Trade Mark) and rinsed several times with a 50 parts methanol/50 parts water mixture. The hydrogenated solution and the rinse liquor were collected and the whole was evaporated to dryness. In this manner, 0.33g of 1D-(1,3,5/2)-1,5-diamino-2,3-cyclohexanediol was obtained in the form of a slightly violet coloured foam. This foam remained homogeneous in a thin layer chromatographic assay of cellulose using a mixture of 2 parts pyridine + 1 part ammonia solution + 2 parts ethanol + 1 part water as solvent.

The 0.33g of diamine so obtained was then taken up in 5 ml of absolute methanol and 3.5 ml of a methanol/10 %-hydrochloric acid solution.

The solution was allowed to stand for 12 hours at 0°C and then the crystals which formed were centrifuged out.

In this manner, 0.2g of 1D-(1,3,5/2)-1,5-diamino-2,3-cyclohexanediol dihydrochloride was obtained in the form of hygroscopic crystals after recrystallisation from a methanol/ether mixture.

M.P. 230°–232°C.

$[\alpha]_D^{25} = + 3.5° \pm 1$ (c=1.17, water).

After crystallisation of the different mother liquors from a methanol/ether mixture, a further quantity of about 0.25g of the desired dihydrochloride was isolated.

Total yield: 90 %.

EXAMPLE 3

Preparation of 1D-(1,3,5/2)-1,5-diazido-2,3-cyclohexanediol a. Preparation of 1L-2,3-anhydro-5-azido-1-0-tosyl-1,2,3/5-cyclohexanetriol (Formula V)

To a solution of 125 mg of 1L-2,3-anhydro-(1,2,3/5)-5-azido-1,2,3-cyclohexanetriol in 3 ml of pyridine, previously cooled were added 280 mg of tosyl chloride. The progress of the reaction was controlled by thin layer chromatography using a 50/50 ethyl acetate/petroleum ether mixture under ultraviolet revealing. After 12 hours, the reaction was finished and extraction with chloroform was carried out. This gave 192 mg of a very, viscous clear oil, which was then purified by thin layer chromatography.

In this manner, 1L-2,3-anhydro-5-azido-1-0-tosyl-1,2,3/5-cyclohexanediol was obtained.

$[\alpha]_D^{25} = + 35°$ (c=1.28, chloroform):

Analysis : $C_{13} H_{15} O_4 SN_3$

|  | C % | H % | N % | S % |
|---|---|---|---|---|
| Calculated | 50.47 | 4.89 | 13.58 | 10.37 |
| Found | 50.26 | 4.90 | 13.33 | 10.39 | b. Preparation of 1L-5-azido-1-0-tosyl-1,2/3,5-cyclohexanetriol (Formula II)

To a solution of 150 mg of 1L-2,3-anhydro-5-azido-1-0-tosyl-1,2,3/5-cyclohexanetriol prepared as described hereabove, in 2 ml of 1,2-dimethoxy-ethane were added 2 ml of a 1.5 N aqueous solution of sulphuric acid. The reaction medium was refluxed for 150 minutes and the progress of the reaction was controlled by thin layer chromatography using a 7/3 ethyl acetate/petroleum ether mixture as solvent. The mixture was then cooled to 0°C and neutralized with an aqueous solution of sodium bicarbonate. After this, the mixture was extracted with ethyl acetate, which provided 102 mg of an oily product presenting several impurity stains which were visible in thin layer chromatography.

In this manner, 1L-5-azido-1-0-tosyl-1,2/3,5-cyclohexanetriol was obtained with a yield of 64 %.

The presence of two hydroxyl groups was confirmed by means of the N.M.R. spectrum of this product after deuteration.

c. Preparation of 1D-(1,3,5/2)-1,5-diazido-2,3-cyclohexanediol (Formula I)

To a mixture of 50 mg of sodium azide and 2 ml of N,N-dimethylformamide were added 100 mg of 1L-5-azido-1-0-tosyl-1,2/3,5-cyclohexanetriol, prepared as described hereabove. The reaction medium was refluxed for 2 hours and the resulting brown solution was poured into iced water. The mixture was extracted with ethyl acetate and the organic phase was washed with water and dried on anhydrous sodium sulphate. The solvent was evaporated out under partial vacuum and 30 mg of brown oil was isolated which, after discolouration with animal charcoal and crystallisation in a chloroform/petroleum ether mixture provided the desired product.

In this manner, 23 mg of 1D-(1,3,5/2)-1,5-diazido-2,3-cyclohexanediol were obtained in the form of crystals melting at 61.5°–63.5°C.

$[\alpha]_D^{25} = + 2° \pm 1$ (c=1.36, methanol).

We claim:

1. A cyclohexanediol derivative corresponding to the general formula:

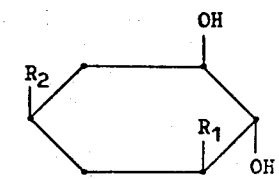

I wherein $R_1$ and $R_2$ each represent a $N_3$ group.

* * * * *

UNITED STATES PATENT OFFICE
CERTIFICATE OF CORRECTION

Patent No. 3,952,027    Dated April 20, 1976

Inventor(s) Andre Cier, Stephan Gero, Alain Olesker & Jean Leboul

It is certified that error appears in the above-identified patent and that said Letters Patent are hereby corrected as shown below:

First page, left column, line 9, below "[21] Appl. No.: 545,799"

the following should appear as follows:

[30] Foreign Application Priority Date

February 15, 1974   France............ 74 05110

Signed and Sealed this

Twentieth Day of July 1976

[SEAL]

Attest:

RUTH C. MASON
*Attesting Officer*

C. MARSHALL DANN
*Commissioner of Patents and Trademarks*